(12) United States Patent
Fillmore et al.

(10) Patent No.: US 11,919,222 B2
(45) Date of Patent: *Mar. 5, 2024

(54) PARISON FOR FORMING BLOW MOLDED MEDICAL BALLOON WITH MODIFIED PORTION, MEDICAL BALLOON, AND RELATED METHODS

(71) Applicant: CLEARSTREAM TECHNOLOGIES LIMITED, Enniscorthy (IE)

(72) Inventors: Paul Fillmore, Gilbert, AZ (US); Allan Ronan, Enniscorthy (IE); Eoin Ryan, Clontarf (IE); Andrew Schaffer, Tempe, AZ (US)

(73) Assignee: CLEARSTREAM TECHNOLOGIES LIMITED, Enniscorthy (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/741,808

(22) Filed: May 11, 2022

(65) Prior Publication Data
US 2022/0266499 A1    Aug. 25, 2022

Related U.S. Application Data

(62) Division of application No. 14/383,764, filed as application No. PCT/US2013/029974 on Mar. 8, 2013, now Pat. No. 11,357,956.
(Continued)

(30) Foreign Application Priority Data

Mar. 9, 2012 (NL) .................................. 2008445

(51) Int. Cl.
B29C 49/22 (2006.01)
A61L 29/18 (2006.01)
(Continued)

(52) U.S. Cl.
CPC .............. *B29C 49/22* (2013.01); *A61L 29/18* (2013.01); *A61M 25/10* (2013.01); *A61M 25/1027* (2013.01); *A61M 25/1029* (2013.01); *B29C 49/0005* (2013.01); *B29D 22/02* (2013.01); *A61M 2025/1031* (2013.01);
(Continued)

(58) Field of Classification Search
CPC .................................. B29C 48/18; B29C 4/20
See application file for complete search history.

(56) References Cited

U.S. PATENT DOCUMENTS 5,270,086 A * 12/1993 Hamlin ............. A61M 25/0009
428/36.9
6,652,568 B1 * 11/2003 Becker .................... A61F 2/958
623/1.2
(Continued)

FOREIGN PATENT DOCUMENTS

| CN | 102209572 A | * | 10/2011 | .......... A61M 25/104 |
| WO | WO-0057816 A1 | * | 10/2000 | .............. A61F 2/958 |
| WO | WO-2010051488 A1 | * | 5/2010 | .......... A61M 25/104 |

*Primary Examiner* — Cachet I Proctor
(74) *Attorney, Agent, or Firm* — Dickinson Wright PLLC; Andrew D. Dorisio

(57) ABSTRACT

A parison for being blow molded into a medical balloon for a catheter includes a first tubular layer having a functional modification and a second tubular layer adapted for bonding with the first tubular layer to form the blow molded balloon. Related methods are also disclosed.

7 Claims, 13 Drawing Sheets

Related U.S. Application Data

(60) Provisional application No. 61/608,908, filed on Mar. 9, 2012.

(51) Int. Cl.
    *A61M 25/10*     (2013.01)
    *B29C 49/00*     (2006.01)
    *B29D 22/02*     (2006.01)
    *B29L 31/00*     (2006.01)

(52) U.S. Cl.
    CPC ............... *A61M 2025/1075* (2013.01); *A61M 2025/1079* (2013.01); *A61M 2025/1086* (2013.01); *B29C 2049/222* (2013.01); *B29L 2031/753* (2013.01); *B29L 2031/7543* (2013.01); *B32B 2535/00* (2013.01)

(56) References Cited

U.S. PATENT DOCUMENTS

| | | | |
|---|---|---|---|
| 6,695,809 B1 * | 2/2004 | Lee | A61M 25/1029 606/108 |
| 6,946,092 B1 * | 9/2005 | Bertolino | A61M 25/1029 264/573 |
| 2003/0004535 A1 | 1/2003 | Musbach et al. | |
| 2006/0226565 A1 | 10/2006 | Hale et al. | |
| 2007/0038290 A1 * | 2/2007 | Huang | B29C 45/0055 623/1.22 |
| 2007/0142771 A1 * | 6/2007 | Durcan | A61M 25/104 604/103.06 |
| 2007/0208365 A1 * | 9/2007 | Lee | A61M 25/0009 606/192 |
| 2009/0204082 A1 * | 8/2009 | Wesselmann | A61M 25/1038 623/1.11 |
| 2010/0036314 A1 * | 2/2010 | Burton | A61M 25/104 604/103.08 |
| 2010/0130926 A1 * | 5/2010 | Lee | B29C 49/22 264/171.28 |
| 2010/0158193 A1 * | 6/2010 | Bates | A61M 25/0108 604/103.08 |
| 2010/0215879 A1 | 8/2010 | Dooley et al. | |
| 2011/0125253 A1 * | 5/2011 | Casanova | A61F 2/06 600/424 |
| 2011/0160661 A1 * | 6/2011 | Elton | A61M 25/10 604/103.06 |
| 2011/0198019 A1 * | 8/2011 | Tilson | A61M 25/0147 156/155 |
| 2013/0030406 A1 * | 1/2013 | Deshmukh | A61P 29/00 604/103.02 |

* cited by examiner

PARISON FOR FORMING BLOW MOLDED MEDICAL BALLOON WITH MODIFIED PORTION, MEDICAL BALLOON, AND RELATED METHODS

This application is a divisional of U.S. application Ser. No. 14/383,764 filed on Sep. 8, 2014, which is a national stage of PCT/US2013/029974 filed on Mar. 8, 2013, which claims priority to U.S. Prov. Appl. No. 61/608,908 and Netherlands Appl. No. 2008445 both filed on Mar. 9, 2012, the disclosures of which are incorporated herein by reference.

TECHNICAL FIELD

This disclosure relates generally to balloons for performing medical procedures, such as angioplasty and, more particularly, to a parison for forming a blow molded medical balloon having a modified portion, such as a layer that is radiopaque, a medical balloon, and related methods.

BACKGROUND OF THE INVENTION

Balloons are routinely used to resolve or address flow restrictions or perhaps even complete blockages in tubular areas of the body, such as arteries or veins. In many clinical situations, the restrictions are caused by hard solids, such as calcified plaque, and require the use of high pressures to compact such blockages. Commercially available balloons employ complex technology to achieve high pressure requirements without sacrificing the profile of the balloon. Besides high pressure requirements, the balloons should also be resistant to puncture, easy to track and push, and present a low profile, especially when used for angioplasty.

In clinical practice, angioplasty balloons are expanded from a deflated, folded state to an expanded state within a vessel to treat a target area, such as a portion of the circumferential inner wall I of a blood vessel V, as shown in FIGS. 1 and 2. The inflation of a balloon 12 with wall 28 is traditionally completed using an X-ray contrast agent CM along dimension DX to provide better visibility under X-ray or other form of radiography R during the interventional procedure, as illustrated in FIGS. 3 and 3a (which shows the intensity measured by a fluoroscope detector plate, FDP). Typically, a 70/30 percent mixture of contrast agent and saline is used to inflate the balloon during an angioplasty procedure.

In general, a desirable goal is to reduce inflation and deflation times required for balloons without sacrificing the profile of the balloons, especially for large volume balloons (which can require up to two minutes of inflation/deflation times with the contrast agent). Because of its relatively high viscosity, it would also be desirable to eliminate, or at least reduce the amount of the contrast agent used in inflation/deflation of the balloons. The use of contrast agent prolongs the inflation/deflation times and also poses the risk of iodine exposure to patients sensitive to iodine. In this regard, a non-radiopaque substance could be used in lieu of the contrast agent, such as for example saline or carbon dioxide, but such substances are invisible during X-ray imaging, and thus do not enhance visibility.

Furthermore, the physician performing the angioplasty procedure should be able to locate the position of the uninflated balloon with accuracy, so that the balloon will be properly positioned once inflated. This is conventionally accomplished by attaching marker bands on the catheter shaft in the region corresponding to the balloon working surface. This "working surface" is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).

Misalignment of the marker bands during placement along the shaft sometimes results in their failure to correspond precisely to the extent of the working surface, as is shown in FIG. 4 (note misalignment amount X between each interior marker band M carried by shaft S and working surface W of balloon 12, which also typically includes a radiopaque tip P at the distal end). Even upon exercising great care to position the markers properly on the underlying shaft in alignment with anticipated boundaries of the working surface when the balloon is inflated, there remains a tendency for mismatch due to several possible factors. One such factor may be the tolerance stack-ups arising as a consequence of the affixation of the balloon to the distal end of the catheter shaft. The balloon also has a tendency to grow in the longitudinal direction when inflated, especially with large and particularly long balloons. Another factor is the tendency of the portion of the catheter shaft within the balloon to bend or flex during inflation. This may lead to misalignment between radiopaque markers fixed to the shaft and the working surface.

Whatever the cause, the resulting misalignment may prevent the clinician from accurately identifying the location of the working surface of the balloon during an interventional procedure. This may lead to a geographic misplacement, or "miss," of the intended contact between the target area T and the working surface W of the balloon 12 (see FIG. 2). It is especially desirable to avoid such an outcome when the balloon is designed to deliver a payload (such as a drug, stent, or both) or a working element to a specified location within the vasculature, since a miss may prolong the procedure (such as, for example, by requiring redeployment of the balloon 12 or the use of another balloon catheter in the case of a drug coated balloon).

Upon deflation, the balloon may also be subject to a phenomenon known as "pancaking." In this condition, the balloon 12 folds down upon itself to a flattened state, as shown in FIG. 5. This situation may cause the balloon to be viewed through fluoroscopy as perhaps still being in the inflated condition, since the full width of the balloon may still be perceived. This can give the clinician the false perception that the balloon remains inflated, when in fact it is not.

Accordingly, the need is identified for a balloon for which the working surface may be identified during an interventional procedure with enhanced precision. The solution would take into account the possible mismatch between fixed locations on the catheter shaft and the balloon to define the working surface, and would operate independent of the position of the portion of the catheter shaft within the balloon. The improved identification may also allow for the better detection of the false perception of deflation caused by pancaking. Overall, procedural efficiency would be enhanced without remarkably increasing cost or complexity, and in a manner that can be applied to many existing catheter technologies without extensive modification.

SUMMARY OF THE INVENTION

An object of the disclosure is to provide a balloon for which the working surface may be identified during an interventional procedure with enhanced precision.

BRIEF DESCRIPTION OF THE DRAWINGS

FIGS. 11-1a and 12-12a show a manufacturing technique for forming the FIG. 10 embodiment;

MODES FOR CARRYING OUT THE INVENTION

The description provided below and in regard to the figures applies to all embodiments unless noted otherwise, and features common to each embodiment are similarly shown and numbered.

Figure 1:
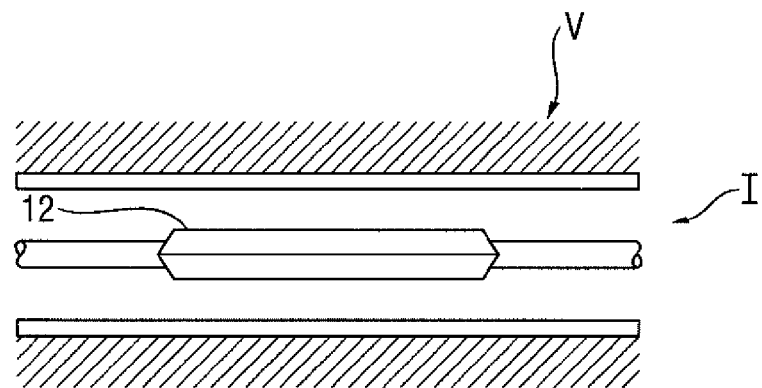
FIGS. 1-9 are illustrative of the background of the invention.
Figure 2:
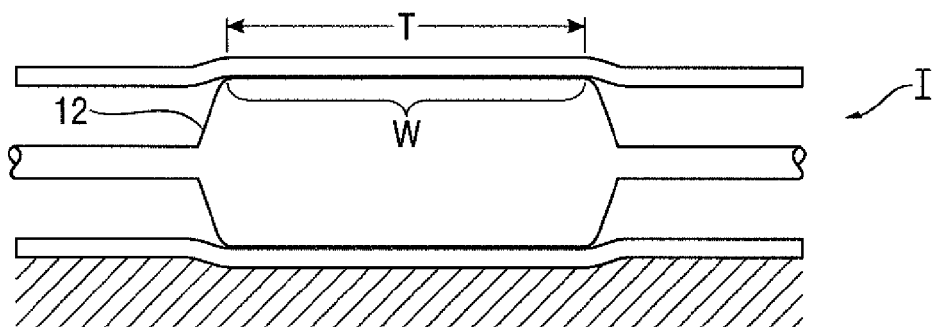
Figure 3:
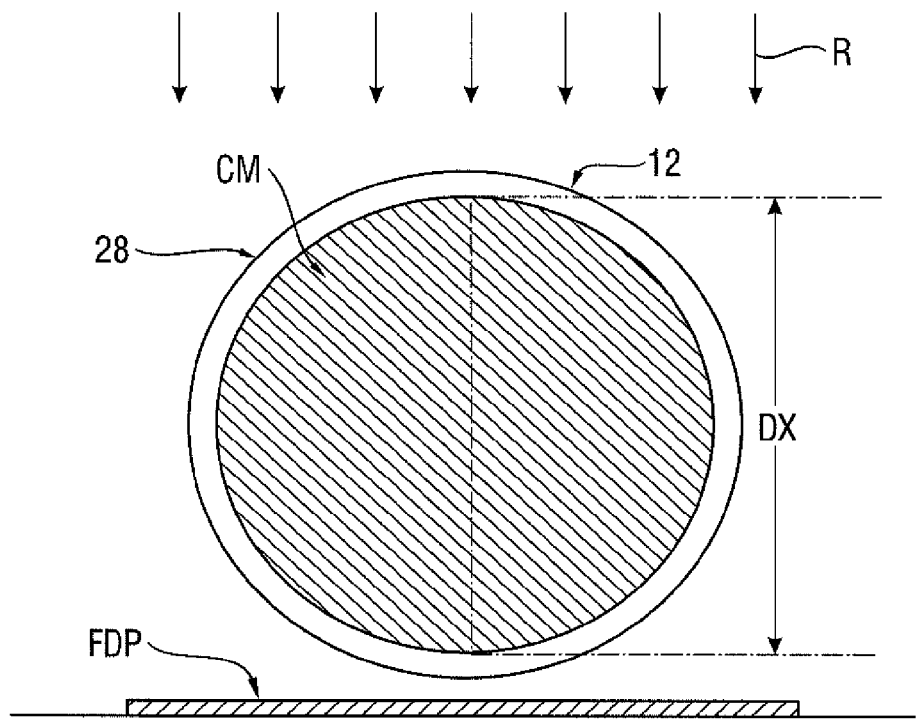
Figure 3A:
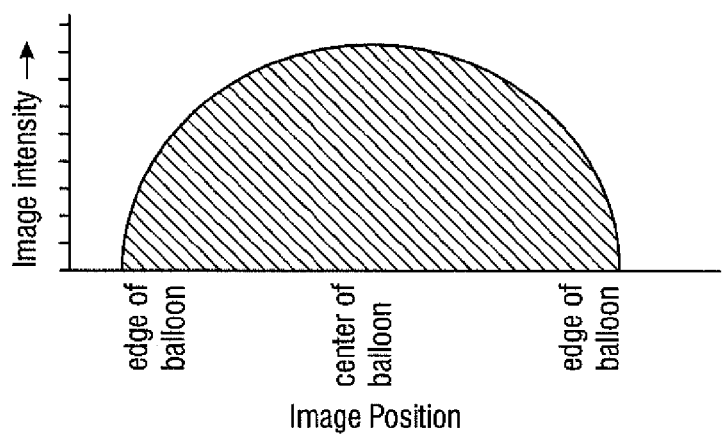
Figure 4:
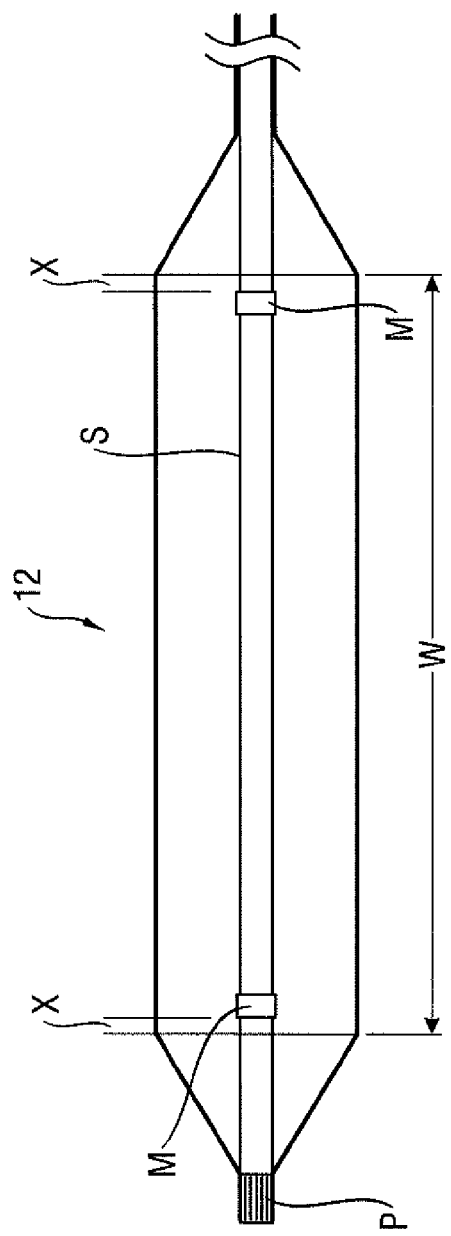
Figure 5:
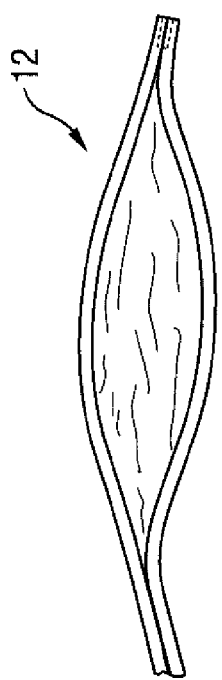
Figure 6:
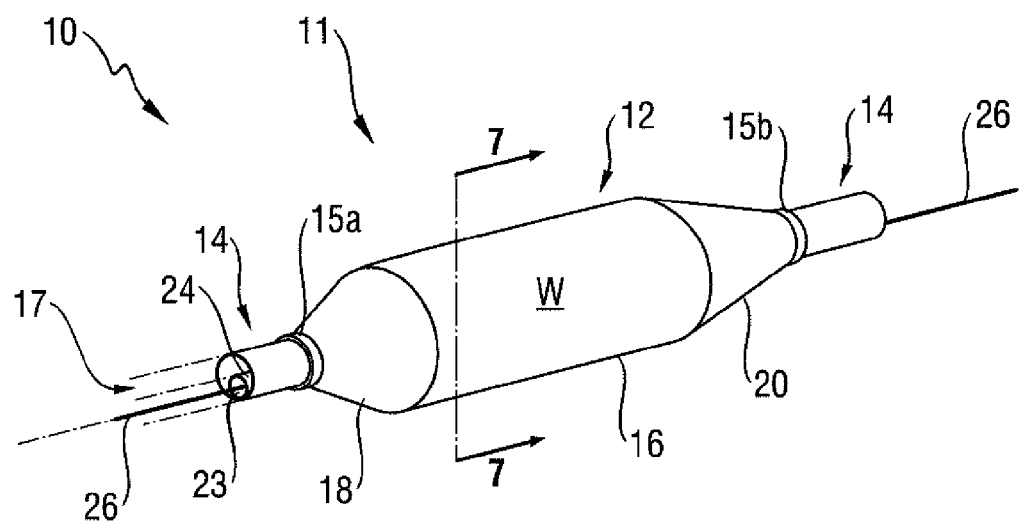
Figure 7:
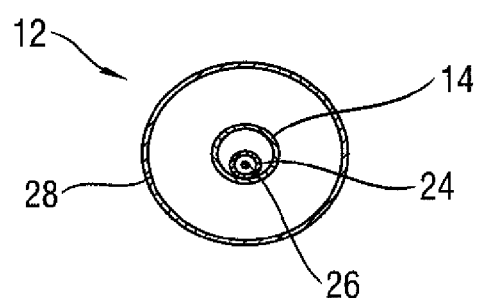
Figure 8:
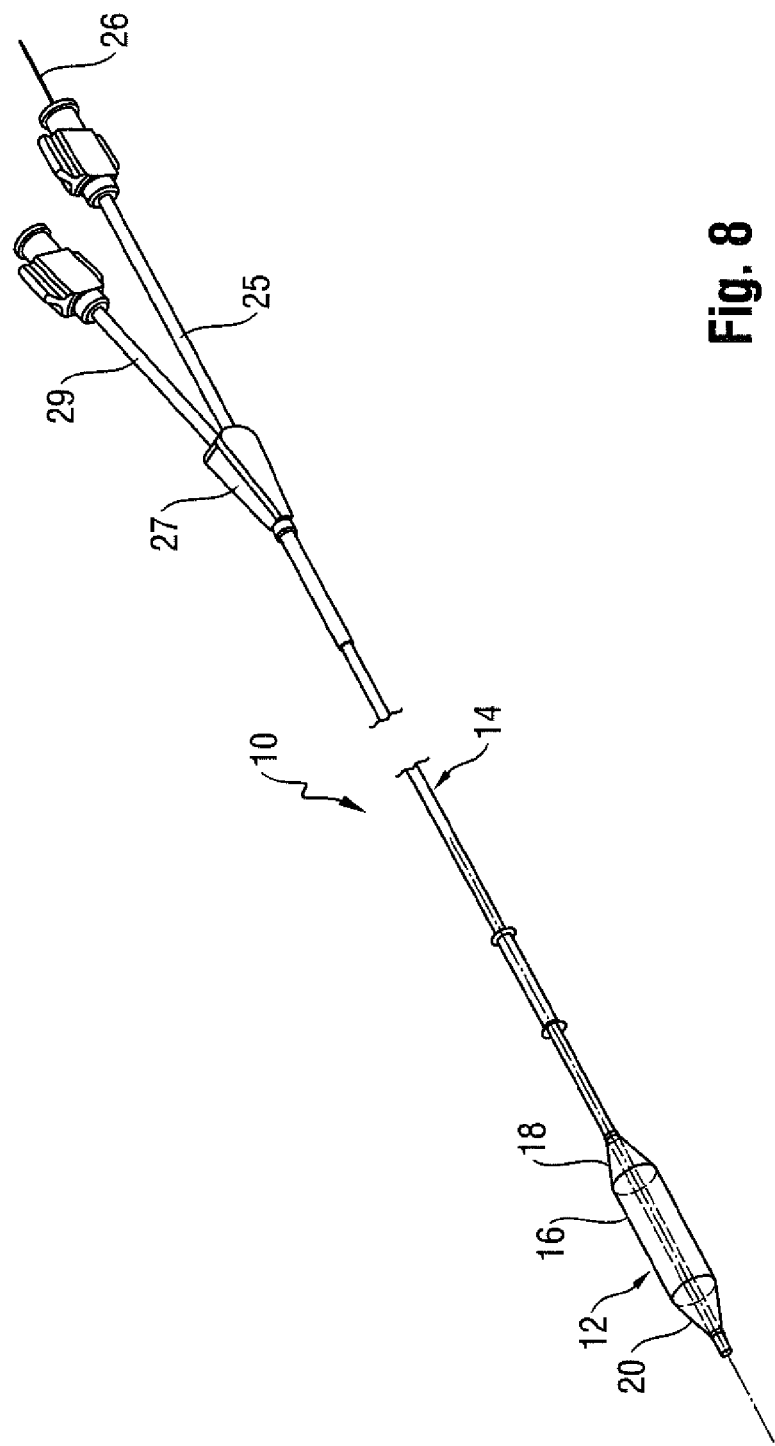

Provided is a catheter 10 having a distal portion 11 with a balloon 12 mounted on a catheter tube 14. Referring to FIGS. 6, 7, and 8, the balloon 12 has an intermediate section 16, or "barrel," and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed at balloon ends (proximal end 15a and distal end 15b) on the cone sections 18, 20 to allow the inflation of the balloon 12 via one or more inflation lumens 17 extending within catheter tube 14 and communicating with the interior of the balloon 12.

Figure 9:
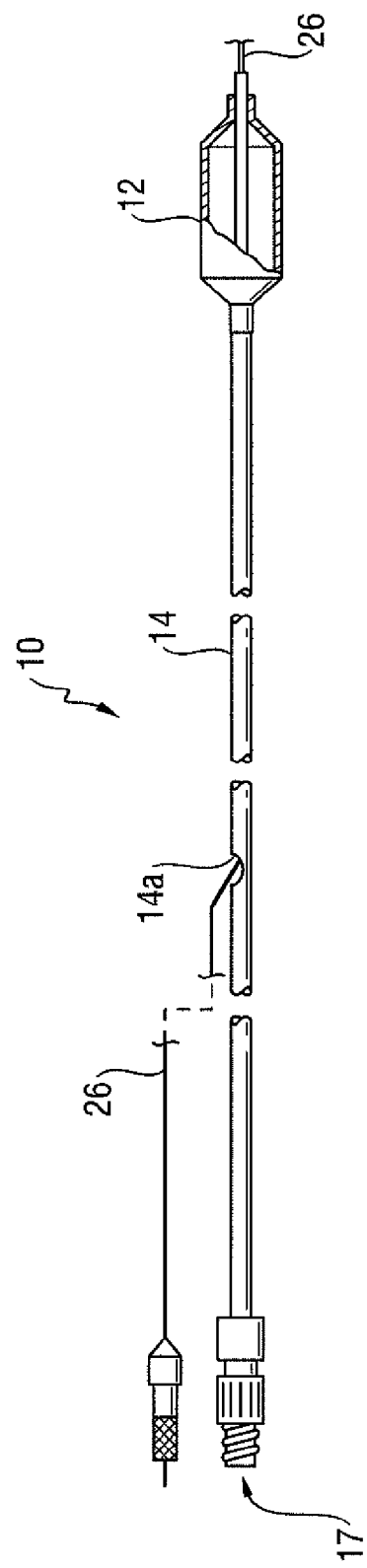

The catheter tube 14 also includes an elongated, tubular shaft 24 forming a guidewire lumen 23 that directs the guidewire 26 through the catheter 10, and along the distal end of which the balloon 12 may be located. As illustrated in FIG. 8, this guidewire 26 may extend through the proximal end of the catheter 10 and a first port 25 of a connector 27 into the lumen 23 to achieve an "over the wire" (OTW) arrangement, but could also be provided in a "rapid exchange" (RX) configuration, in which the guidewire 26 exits a lateral opening 14a closer to the distal end (see FIG. 9) or else is fed through the tip at a passage distally of the balloon 12 ("short" RX; not shown). A second port 29 may also be associated with catheter 10, such as by way of connector 27, for introducing a fluid (e.g., saline, a contrast agent, or both) into the interior compartment of the balloon 12 via the inflation lumen 17.

Balloon 12 may include a single or multi-layered balloon wall 28 forming the interior for receiving the inflation fluid. The balloon 12 may be a non-compliant balloon having a balloon wall 28 that maintains its size and shape in one or more directions when the balloon is inflated. Examples of non-compliant balloons may be found in U.S. Pat. No. 6,746,425 and Publication Nos. US 2006/0085022, US 2006/0085023, and US 2006/0085024, the disclosures of which are hereby incorporated herein by reference. The balloon 12 in such case also has a pre-determined surface area that remains constant during and after inflation, also has a pre-determined length and pre-determined diameter that each, or together, remain constant during and after inflation. The balloon 12 could also be semi-compliant or compliant instead, depending on the particular use.

In order to provide for enhanced locatability during an interventional procedure, the balloon 12 may have a modified portion having a radiopaque quality. In one embodiment, this radiopaque quality is provided in a manner that allows for a clinician to differentiate, with relative ease and high precision, one portion of the balloon 12 from another (such as, but not limited to, the barrel section 16 including the working surface W from the cone sections 18, 20). This helps the clinician ensure the accurate positioning of the balloon 12 and, in particular, a portion of or the entire working surface W, at a specified treatment location, which may be especially desirable in the delivery of drugs via the balloon working surface W, as outlined in more detail in the following description.

Figure 10:
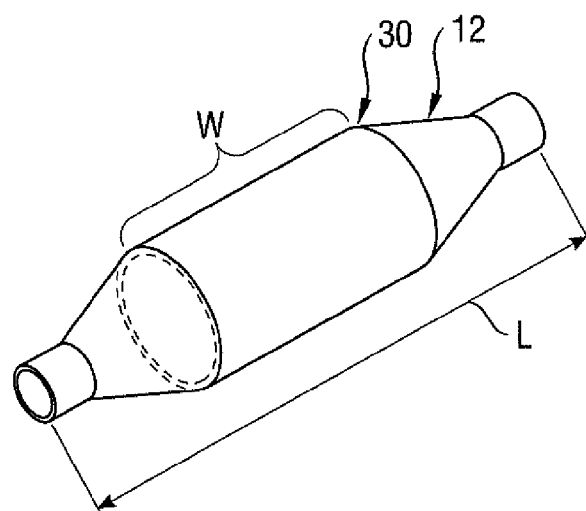
FIG. 10 illustrates a first embodiment according to the disclosure.

In one embodiment, and with initial reference to FIG. 10, the radiopaque quality is achieved by providing one or more at least partially radiopaque markings 30. The marking or markings 30 may be provided along the balloon 12 to create a defined portion as the working surface W, as contrasted with the full length L of the balloon. For example, a marking 30 extend along the balloon 12 in a longitudinal direction along the barrel section 16 and over the entire circumference of the working surface W. Alternatively, the marking 30 may extend over only a portion of the working surface W, or may extend over only a different part of the balloon 12 (such as the cone sections 18, 20), as outlined further in the following description.

Figure 11:
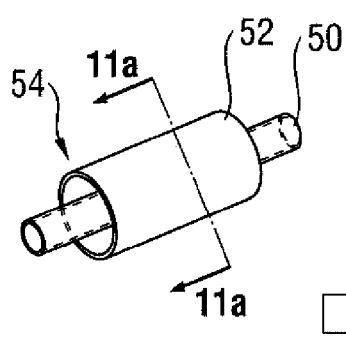
Figure 12:
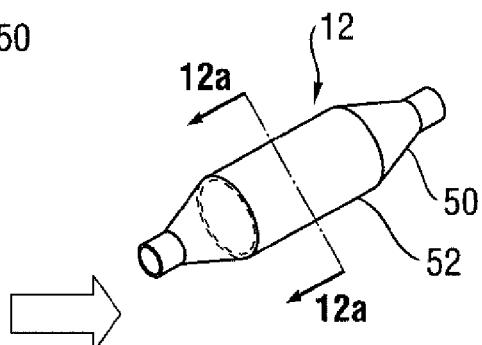
Figure 11A:
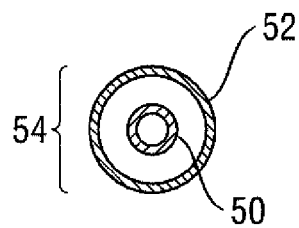
Figure 12A:
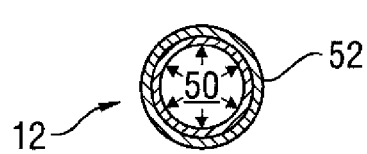
Figure 18:
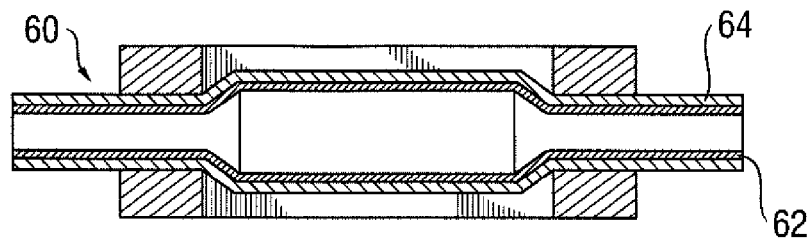
FIGS. 18-21 show still further embodiments.

This marking 30 may be provided during a process used to form the balloon 12 having the desired shape created by a multi-layered wall 28. In particular, a first tube 50 comprising a thin layer of material (such as a polymer), may be inserted within a second tube 52, to form a parison 54, as shown in FIGS. 11 (perspective view) and 11a (cross-section). The second tube 52 may also comprise a compatible polymeric material, but could also be formed of a different material (such as metal, including possibly a film). The second tube 52 includes the one or more radiopaque markings 30, which may correspond in length to the barrel section 16 of the finished balloon, as shown in FIG. 11 (but the second tube could extend the entire length of the balloon 12, as discussed below and illustrated by inner tube 62 in FIG. 18). The first, inner tube 50 may then be expanded to form a multi-layered balloon 12 (FIG. 12), with the second, outer tube 52 thus forming a radiopaque outer sleeve, as shown in the cross-sectional view of FIG. 12a.

Figure 13:
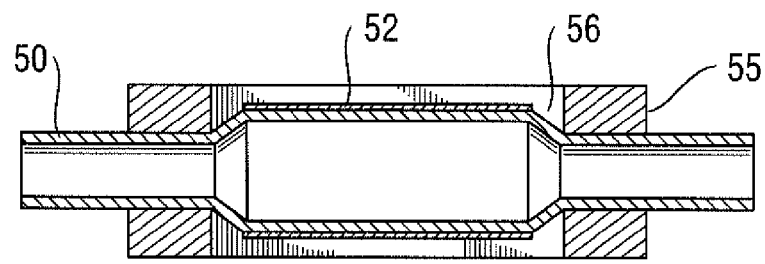
FIGS. 13 and 14 further shown manufacturing techniques.

Turning to FIG. 13, it can be understood that this processing may be achieved using a blow mold 54 having separable portions forming a mold cavity 56 corresponding in shape to the desired shape of the balloon. The outer tube 52 may be pre-positioned in the mold cavity 56, including possibly within a correspondingly shaped recess formed along one or more of the interior surfaces of the mold 55. The inner tube 50 may then be expanded using heat and pressure to form the balloon 12 with the desired shape, and having the outer tube 52 intimately bonded to it.

Figure 14:
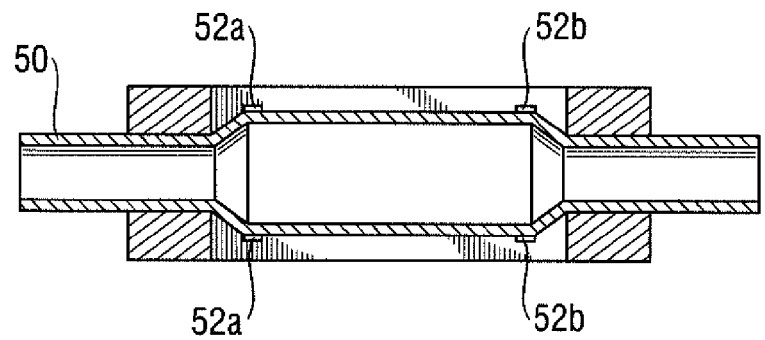
Figure 19:
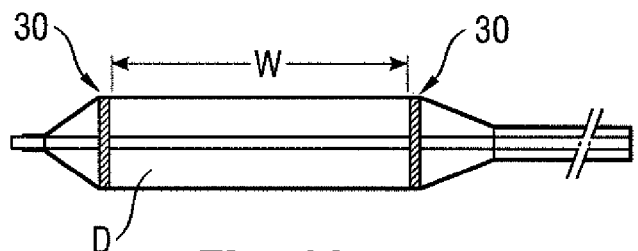

FIG. 14 shows that, instead of a single tube 52, two spaced tubes, such as radiopaque collars 52a, 52b, may be provided on the inner tube 50 in order to provide spaced markings 30 on the finished balloon 12 (see FIG. 19). Like tube 52, these collars 52a, 52b may be pre-positioned in the mold cavity 56 so as to receive the inner tube 50 when inserted. As noted above for tube 52, the collars 52, 52b may be comprised of a thin flexible, material (e.g., a polymer, such as nylon)

compatible with the material (e.g., a polymer, such as nylon) of the adjacent layer formed by tube 50, but could also be made of different materials, such as one or more metal foils. Upon expanding the inner tube 50, the collars 52a, 52b are intimately bonded to form a balloon 12 with spaced, radial markers, which as the result of the positioning at predetermined locations in the mold cavity 56 may align precisely with the edges of the working surface W.

The markings 30 may be provided on the tube 52 (or tubes 52a, 52b) in various ways. For example, the markings 30 may be provided by applying a radiopaque material to the tube 52 at the desired location in any shape, pattern or form (including possibly alphanumeric characters to provide information that can be perceived under fluoroscopy, such as a length, diameter, logo, trademark, rated burst pressure, or balloon type). This may be done by inking, spraying, printing, or painting the radiopaque material in fluid form on the surface of the tube 52 (possibly with the application of a mask or the like, in which case the techniques of dipping or rolling in the radiopaque material to form the desired coating could be used). Alternatively, the marking 30 may be embedded in the tube 52, including for example by providing it as part of a film, or in a bonding agent or adhesive used to bond multiple layers together to form the tube 52 (see, e.g., U.S. Patent Application Publication No. 2011/0160661, the disclosure of which is incorporated herein by reference). The marking 30 may be provided during the process of fabricating the tube 52, such as for example during a co-extrusion process. Examples of such techniques are described in a co-pending application filed on the same date as this application, "MEDICAL BALLOON WITH COEXTRUDED RADIOPAQUE PORTION," listing as inventors Paul Fillmore, Justin Hall, Pat Byrne, Margo Underwood, the disclosure of which is incorporated herein by reference.

Figure 15:
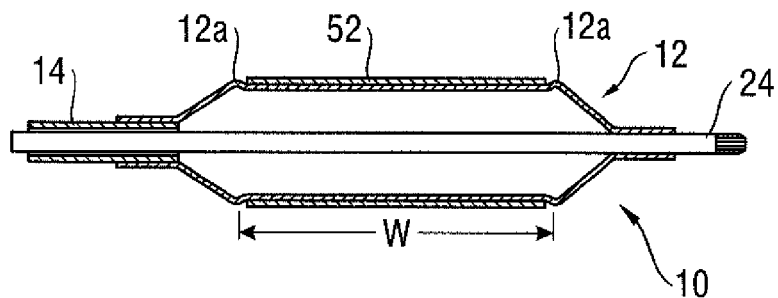
FIG. 15 illustrates a further embodiment according to the disclosure.
Figure 16:
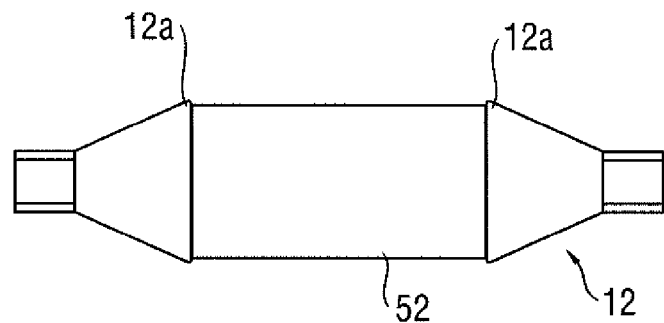
FIGS. 16 and 17 illustrate another embodiment according to the disclosure.
Figure 17:
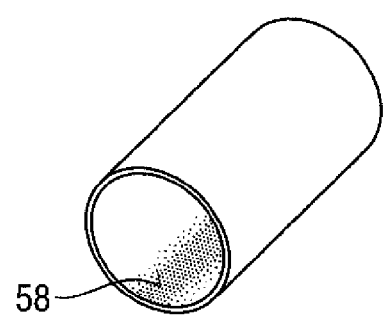

As perhaps best understood with reference to FIGS. 15 and 16, the mold cavity may be adapted to form the balloon 12 with the desired shape and appearance, and could also be adapted to form shoulders 12a on the balloon 12 once blown. These shoulders 12a may help to retain the outer tube 52 providing the modified portion of the balloon 12 against movement in the longitudinal direction, and thus help to ensure that it remains positioned at the desired location (again, in one embodiment, aligned with the full extent of the working surface W). Additionally or alternatively, as shown in FIG. 17, the inner surface of the outer tube 52 may be adapted for frictionally engaging the outer surface of the tube 50, such as by providing a roughened or textured surface 58.

Additionally or alternatively, an adhesive may be used to improve the bond between the tubes 50, 52. This adhesive may be provided on either tube prior to blow molding. The adhesive may also optionally be provided with a radiopacifier in order to enhance the radiopaque quality of the balloon 12 (see, e.g., U.S. Patent Application Publication No. 2011/0160661).

Another embodiment involves forming the balloon 12 with a modified portion by blow molding a multi-layered parison, wherein at least one of the layers of the parison comprises a radiopaque material. Thus, for example, a parison 60 in this embodiment may include an inner layer comprising a radiopaque film 62, and an outer layer 64 comprising a traditional film that is not made radiopaque by an additive. The blow molding process expands the parison 60 to thus form a balloon 12 having a radiopaque quality corresponding to the length of the inner layer including radiopacifier, which may be the full length L of the balloon 12.

Balloons 12 that incorporate coatings comprising drugs to be applied to the vasculature may also benefit from the above-referenced embodiments. For example, as shown in FIG. 19, a balloon 12 including a defined working surface W, such as by providing radiopaque markings 30 at the transitions between the barrel section 16 and cone sections 18, 20, may include a portion coated with such a drug D, such as one designed for achieving a desired therapeutic effect when applied to the interior of the vessel. The radiopaque marking 30 may also correspond to the location of the drug D on the balloon 12, such as along the entire working surface W or only a portion of it. The drug D may be applied to the inflated balloon as part of the manufacturing process, and prior to folding for insertion in the vasculature. The clinician may thus with the benefit of a fluoroscope determine the precise positioning of the working surface W prior to inflating the balloon 12 in the vasculature to deliver the drug D to the desired location and provide the desired treatment regimen.

Figure 20:
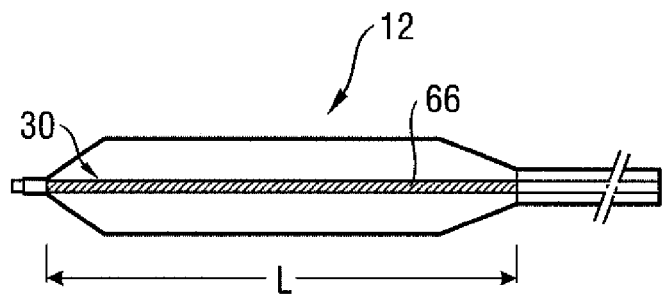
Figure 21:
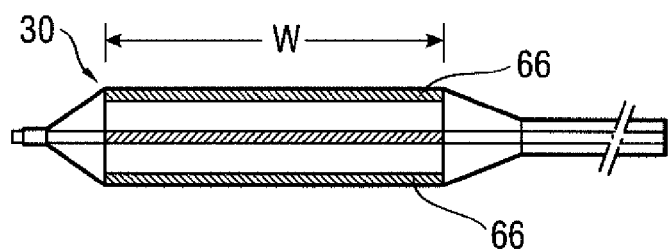

The markings 30 may also be provided as one or more longitudinal strips 66 that do not extend along the entire circumference of the balloon 12, as shown in FIGS. 20 and 21. This may be achieved by providing one or both of the layers 62, 64, or the tube 52, with radiopaque material corresponding to the strips 66, such as by a co-extrusion process. Additional details are provided in a concurrently filed patent applications entitled, "MEDICAL BALLOON WITH RADIOPAQUE IDENTIFIER FOR PRECISELY IDENTIFYING THE WORKING SURFACE," for inventors Sean Wall, Pat Byrne, Robert Righi, Angela Crall, Paul Wales, and Allan Ronan, and "MEDICAL BALLOON WITH RADIOPAQUE END PORTION FOR PRECISELY IDENTIFYING A WORKING SURFACE LOCATION," for inventors Sean Wall, Scott Randall, Robert Righi, Angela Crall, the disclosures of which are incorporated herein by reference. The presence of plural spaced markings 30 in this manner may also help to distinguish between the inflated condition (in which the markings are spaced), and the properly deflated condition, as the markings would be closer to each other when the balloon is folded.

Figures 22, 22A:
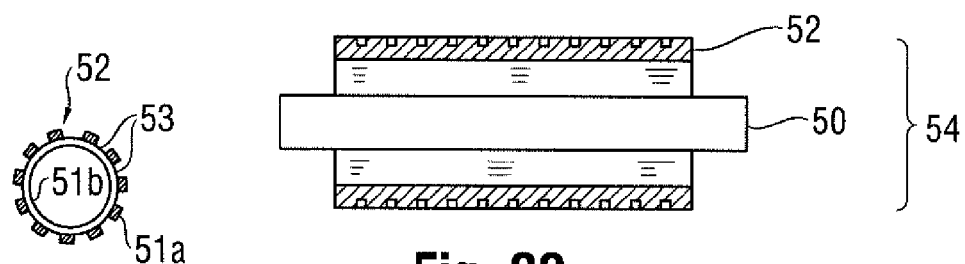
FIGS. 22 and 22a are cross-sectional side and end views of another embodiment.

In another embodiment, the blow molding operation may be arranged to create a balloon 12 with a different type of modified layer. For example, in FIG. 22, an insert 52 may be provided with a functional modification, such as an outer surface that is textured or etched, and associated with an inner tube 50. The insert 52 could be made partially or fully radiopaque if desired (see, e.g., FIG. 10), but such is considered optional. In one embodiment, a multi-layered insert 52 may be provided with an outer radiopaque layer 51a and an inner support layer Sib that is not enhanced with a radiopacifier and exposed by the openings 53 formed by etchings in the outer layer (see FIG. 22a). This may create a particular pattern under fluoroscopy, which may allow for the detection of the locations on the balloon 12 where a drug is present (either on the etched portions or the unetched portions, as desired, which again may correspond to the working surface W).

Figure 23:
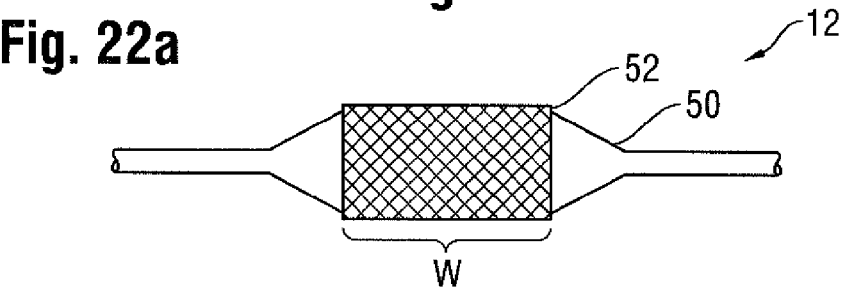
FIG. 23 is a side view of a balloon catheter formed according to one aspect of the disclosure.

In any case, on blow molding the resulting parison 54 into a corresponding mold 55 (see FIGS. 13 and 14), a balloon 12 may be formed having an etched or textured outer surface layer 28a of the balloon wall 28. This layer 28a may extend along the entire working surface W, as shown in FIG. 23, or any portion of it. In the case of etching, texturing, or other surface features, the material forming the insert 52 should have a sufficiently high melt flow index such that the features are not caused to disappear as the result of the heat and pressure created during the blow molding process.

Figure 24:
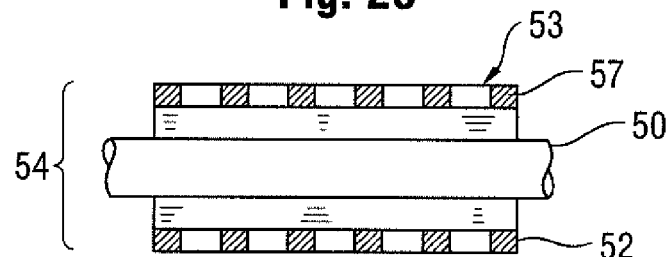
FIGS. 24 and 25 show a further embodiment.

Another example for creating a balloon 12 with a modified layer is to provide an insert 52 with one or more openings. For example, as shown in FIG. 24, the insert 52 may be provided as a reticulated or fenestrated body, such as a mesh, screen or lattice having a plurality of crossing members 57 forming openings 53. The body 52 may be tubular in form, as shown, and could comprise more than one piece or part (similar to collars 52a, 52b). As above, the material forming the insert 52 should have a sufficiently high melt flow index such that the features are not caused to disappear as the result of the heat and pressure created during the blow molding process.

When arranged to form a parsion 54 and blow molded together, the insert 52 bonds to an inner tube 50 and forms an outer layer of the finished balloon 12. In the case of an insert 52 as shown, the openings 53 expose the balloon wall 28, which may be adapted to form the modified layer (such as by being radiopaque). The body 52 may extend along the entire working surface W, and may optionally be fully or partially radiopaque. Alternatively, the body 52 may be provided with a coating, such as in the form of a drug or an agent providing enhanced lubricity.

Figure 25:
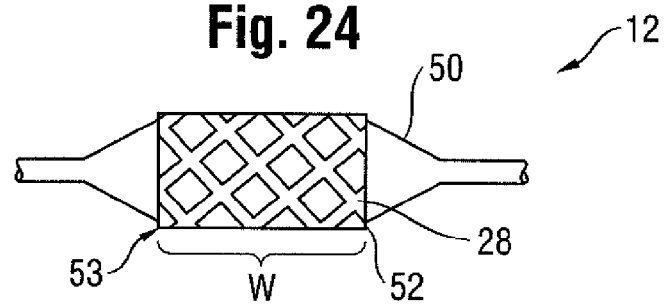
Figure 26:
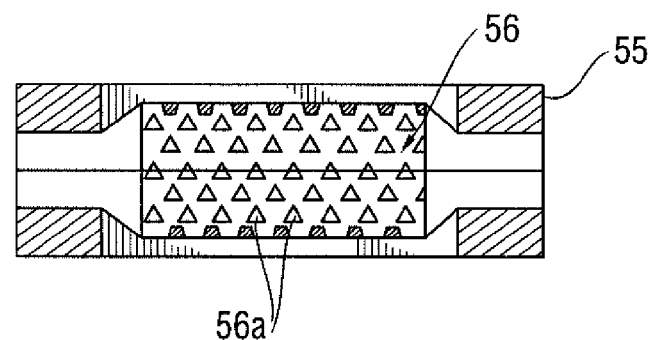
FIGS. 26-28 show still a further embodiment.

It is also possible to modify the mold 55 to provide a surface treatment on the finished balloon 12. For example, as shown in FIG. 25, the inner surfaces of the mold cavity 56 may be provided with a textured pattern 56, such as by etching, engraving, or the like, so as to form inwardly directed projections. This includes along the portions corresponding to the working surface W of the balloon 12 (e.g., the barrel section). When a parison 54 (which may be a single layer of material), is then expanded in the mold cavity 56 (FIG. 26), the surface of the resulting balloon 12 is provided with a corresponding pattern in the form of an impression of the pattern in the mold 55. In other words, the projections forming the pattern 56a in the mold form depressions in the outer surface of the balloon wall 28.

Figure 27:
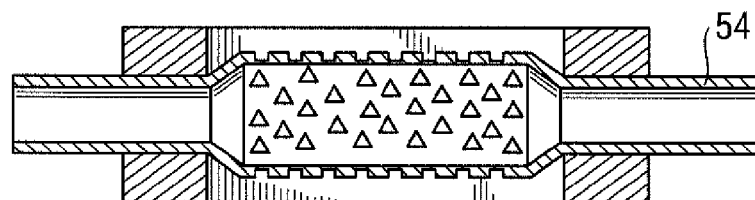
Figure 28:
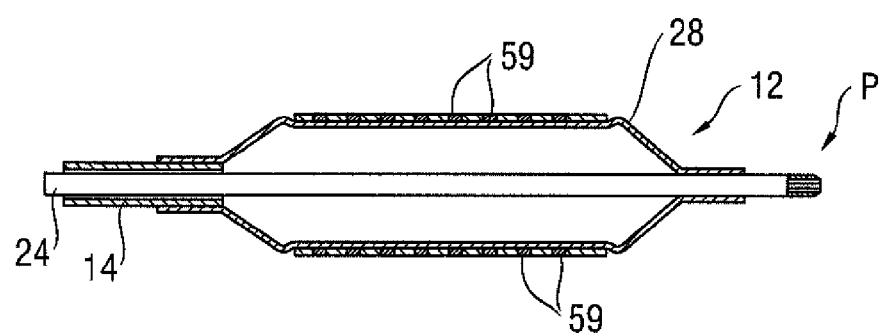

An option in this embodiment is to deposit a material within the mold cavity 56 to partially or completely fill any spaces or gaps formed in the pattern 56a, such as for example a radiopacifier 59. As shown in FIGS. 27 and 28, the balloon 12 resulting from blow molding using a mold 55 with this type of pattern 56a with a filler would thus have a surface layer modified to including the selected filler material (which in the case of a radiopacifier 59 would make the surface partially radiopaque, as shown by the darkened portions of the balloon wall 28 in FIG. 28). The depositing of the material within the mold 55 may be done by injection through an internal passageway opening within the cavity 56, either before or during the molding process, including possibly by spraying the filler material within the mold cavity 56 (such as when the mating portions forming the mold 55 are separated to expose the surface pattern 56a).

Examples of radiopaque materials include, but are not limited to, finely divided tungsten, tantalum, bismuth, bismuth trioxide, bismuth oxychloride, bismuth subcarbonate, other bismuth compounds, barium sulfate, tin, silver, silver compounds, rare earth oxides, and many other substances commonly used for X-ray absorption. The polymer used for making a film, possible with a radiopaque material, may be any polymeric material which can be loaded with radiopacifier and formed into a sufficiently thin film. Examples of polymers include thermoplastic and thermoset polymers. Some examples of thermoplastic polymers include, but are not limited to, polyurethanes, polyamides (nylon 11, nylon 12), polyether-polyamide copolymers such as PEBAX, polyethylene terephthalate or other polyesters, polyvinyl acetate, polyvinyl chloride, and many other thermoplastic materials useful for making films. Some examples of thermoset polymers include, but are not limited to, crosslinked polyurethanes, polyureas, epoxies, acrylics, silicones, and many other thermoset materials that can be formed into thin structures, including films. Any adjacent structures to be bonded, such as tubes 50, 52 or layers 62, 64, may be formed of compatible materials, which may avoid additional processing or the inclusion of a compatibilizer, tie layer or the like.

The invention may be understood with reference to the following items:

1. A parison for being blow molded into a medical balloon for a catheter, comprising
    a first tubular layer having a functional modification; and
    a second tubular layer adapted for bonding with the first tubular layer to form the blow molded balloon.
2. The parison of item 1, wherein the first layer is external to the second layer.
3. The parison of item 1, wherein the first layer is internal to the second layer.
4. The parison of any of the foregoing items, wherein the radiopaque portion comprises a strip.
5. The parison of item 4, wherein the strip comprises a circumferential band.
6. The parison of item 4 or 5, wherein the strip extends between a first end and a second end of the first layer.
7. The parison of any of the foregoing items, wherein the first tubular layer is spaced from the second tubular layer.
8. The parison of any of the foregoing items, wherein the functional modification is selected from the group consisting of an added radiopacifier, a surface pattern, an etching, one or more perforations, and combinations of the foregoing.
9. A medical balloon comprising a generally cylindrical barrel section forming a working surface, and an at least partially radiopaque tube positioned over the barrel section and extending substantially along the working surface.
10. The balloon of item 9, further including first and second shoulders adjacent the proximal and distal ends of the radiopaque tube.
11. The balloon of item 9 or 10, wherein the entire tube is radiopaque.
12. The balloon of any of items 9 to 11 formed by the parison of any of items 1 to 8, comprising: a tubular, inflatable body comprising a wall, the body including first and second generally conical ends and the generally cylindrical barrel section between the generally conical ends and providing the working surface.
13. The balloon of item 12, wherein the first layer extends from the first end to the second end of the balloon.
14. The balloon of item 12, wherein the first layer extends along only the working surface.
15. The balloon of any of items 12 to 14, wherein the first layer extends along an entire circumference of a portion of the wall.
16. The balloon of any of items 12 to 15, wherein the first layer extends along the full circumference of the wall.
17. The balloon of any of items 12 to 16, wherein the wall includes first and second spaced shoulders, and wherein the first layer is positioned between the shoulders.
18. The balloon of any of items 12 to 17, wherein the first and second layers both extend from a first end to a second end of the balloon.

19. A method of manufacturing an at least partially radiopaque balloon, comprising: blow molding a first layer of a material having a functional modification and a second layer of material together to form the balloon.
20. The method of item 19, wherein the blow molding step comprises providing the first layer along an inner surface of the second layer.
21. The method of item 19, wherein the blow molding step comprises providing the first layer along an outer surface of the second layer.
22. The method of any of items 19 to 21, further including the step of providing the first layer of material that is shorter that the second layer of material in a longitudinal direction.
23. The method of any of items 19 to 22, further including the step of providing the first layer with a radiopaque portion in the form of at least one strip.
24. The method of any of items 19 to 23, further including the step of providing the first layer with a substantially continuous radiopacity.
25. The method of any of items 19 to 24, further including the step of providing the first layer with the functional modification selected from the group consisting of an added radiopacifier, a surface pattern, an etching, one or more perforations, and combinations of the foregoing.
26. A method of manufacturing a medical balloon using a mold having a mold cavity, comprising: blow molding a parison at least partially within the mold cavity of the mold to form a balloon having a modified outer portion along a working surface of the balloon.
27. The method of item 26, wherein the blow molding step is preceded by the step of providing a material for forming the modified portion in the blow mold.
28. The method of item 26 or 27, wherein the blow molding step is preceded by the step of providing a tube for forming the modified portion in the blow mold.
29. The method of any of items 26 to 28, wherein the blow molding step is preceded by the step of providing a fenestrated tube for forming the modified portion in the blow mold.
30. The method of any of items 26 to 29, wherein the blow molding step is preceded by the step of providing a reticulated tube for forming the modified portion in the blow mold.
31. The method of any of items 26 to 30, wherein the mold cavity includes a surface pattern, and the blow molding step creates the modified portion by contacting the parison with the surface pattern.
32. The method of any of items 26 to 31, wherein the mold cavity includes a surface pattern and a filter material, and the blow molding step creates the modified portion by contacting the parison with the surface pattern and the filler material.
33. The method of any of items 26 to 32, wherein the mold cavity includes a surface pattern and a radiopaque material, and the blow molding step creates the modified portion by contacting the parison with the surface pattern and the radiopaque material.
34. A method for forming a balloon, comprising:
blow molding a radiopaque material to form the balloon.

The subject matter of each of the paragraphs below citing a balloon or a catheter can be part of a balloon or a catheter respectively that is cited in any of the other paragraphs:
1.1 A balloon catheter, comprising: an elongated, tubular shaft extending in a longitudinal direction, said shaft having a proximal end and a distal end; and an inflatable balloon supported along the distal end of the shaft, the balloon when inflated including first and second spaced conical end sections and a working surface between the conical sections, the balloon further including at least one radiopaque marking identifying the transition from the conical end section to the working surface.
1.2 The catheter of paragraph 1.1, wherein the at least one radiopaque marking comprises a first radiopaque marking at a first transition between the first conical end section and the working surface, and further including a second radiopaque marking at a second transition between the second conical end section and the working surface.
1.3 The catheter of any of the foregoing paragraphs, wherein the at least one marking comprises a strip.
1.4 The catheter of any of the foregoing paragraphs, further including a plurality of radiopaque markings in the form of strips.
1.5 The catheter of paragraph 1.4, wherein the strips extend at least partially in a longitudinal direction between the first and second conical end sections.
1.6 The catheter of paragraphs 1.4 or 1.5, wherein the strips comprise annular bands.
1.7 The catheter of any of the foregoing paragraphs, wherein at least two spaced radiopaque markings are provided on each conical end section, including one adjacent a distal portion and a proximal portion of each conical end section.
1.8 The catheter of any of the foregoing paragraphs, wherein the balloon includes a barrel section between the first and second conical end sections, and further including a plurality of radiopaque markings on the barrel section.
1.9 The catheter of any of the foregoing paragraphs, wherein the marking comprises a first pattern on the conical end sections and further including a second, different pattern on the working surface.
1.10 The catheter of any of the foregoing paragraphs, wherein the at least one marking is selected from the group consisting of a pattern, a strip, a brand, a logo, a letter, a number, a word, or combinations thereof.
1.11 The catheter of any of the foregoing paragraphs, wherein the identifier comprises a scale.
1.12 The catheter of any of the foregoing paragraphs, wherein the balloon includes a drug.
1.13 The catheter of paragraph 1.12, wherein the drug corresponds to the location of the radiopaque marking.
1.14 The catheter of paragraph 1.12, wherein the drug corresponds to other than the location of the radiopaque marking.
1.15 The catheter of paragraph 1.12, wherein the radiopaque marking comprises the drug formulated to include a radiopacifier.
1.16 A balloon having a drug carried on a working surface of the balloon wall and a radiopaque identifier identifying the location of the drug on the balloon.
1.17 The balloon of paragraph 1.16, wherein the radiopaque identifier comprises a radiopaque material mixed with a formulation comprising the drug.
1.18 The balloon of paragraph 1.16, wherein the working surface is along a barrel section of the balloon, and the radiopaque identifier is on one or both cone sections of the balloon.
2.1 A balloon catheter, comprising: an elongated, tubular shaft extending in a longitudinal direction, said shaft having a proximal end and a distal end; and an inflatable balloon supported along the distal end of the shaft, the balloon when inflated including a generally cylindrical barrel section forming a working surface, and generally conical end sections that do not form a part of the working surface, the balloon further including at least one radiopaque identifier for indicating the relative position of the working surface, said identifier being provided on at least one of the conical end sections of the balloon so as to define the extent of the working surface.

2.2 The catheter of paragraph 2.1, wherein the identifier comprises a marking.

2.3 The catheter of paragraph 2.1 or 2.2, wherein a first marking is provided at a first transition between the first conical section end section and the working surface and a second marking is provided at a second transition between the second end section and the working surface.

2.4 The catheter of paragraph 2.2 or 2.3, wherein the marking comprises a strip.

2.5 The catheter of any of the foregoing paragraphs, wherein the identifier comprises a longitudinal strip extending between an end of the balloon and the barrel section.

2.6 The catheter of any of the foregoing paragraphs, further including a plurality of identifiers.

2.7 The catheter of paragraph 2.6, wherein each of the plurality of identifiers comprises a longitudinally extending strip.

2.8 The catheter of paragraph 2.6 or 2.7, wherein the identifiers comprise annular bands.

2.9 The catheter of paragraph 2.6 or paragraph 2.8 as dependent on paragraph 2.6, wherein the identifiers comprise longitudinally extending strips.

2.10 The catheter of any of the foregoing paragraphs 2.1 to 2.9, wherein at least two spaced radiopaque identifiers are provided on each end section.

2.11 The catheter of any of the foregoing paragraphs 2.1 to 2.10, further including at least one radiopaque identifier on the barrel section.

2.12 The catheter of any of the foregoing paragraphs 2.1 to 2.11, wherein the identifier is a first identifier comprising a first pattern, and further including a second identifier comprising a second, different pattern.

2.13 The catheter of any of the foregoing paragraphs 2.1 to 2.12, wherein the identifier includes at least one letter or number.

2.14 The catheter of any of the foregoing paragraphs 2.1 to 2.13, wherein the identifier comprises a logo.

2.15 The catheter of any of the foregoing paragraphs 2.1 to 2.14, wherein the identifier comprises a scale.

2.16 The catheter of any of the foregoing paragraphs 2.1 to 2.15, further including a drug on the balloon.

3.1 An inflatable balloon for use in connection with a catheter, comprising: an inflatable body including a working surface extending in a longitudinal direction between a first end and a second end, the body having at least one radiopaque identifier provided along the body for identifying at least a first end of the working surface, the radiopaque identifier having a first radiographic quality for identifying the location of the first end of the working surface and a second radiographic quality at a location other than at the first end of the working surface.

3.2 The balloon of paragraph 3.1, wherein the second radiographic quality is provided for identifying the second end of the working surface.

3.3 The catheter of paragraph 3.2, wherein the first radiographic quality and the second radiographic quality are substantially the same.

3.4 The balloon of paragraph 3.1, wherein the radiopaque identifier comprises a marking.

3.5 The balloon of paragraph 3.1, wherein the radiopaque identifier follows a generally helical path from the first end to the second end of the working surface.

3.6 The balloon of paragraph 3.1, wherein the identifier comprises a plurality of helical identifiers extending along the working surface.

3.7 The balloon of paragraph 3.1, wherein the identifier comprises a radiopaque filament.

3.8 The balloon of paragraph 3.7, wherein the filament is wound helically along at least a portion of the working surface of the balloon.

3.9 The balloon of any of the foregoing paragraphs 3.1 to 3.8, further including a drug on the balloon.

3.16 A balloon for use in connection with a catheter, comprising: a body having an outer surface and at least one winding extending along the outer surface of the balloon, said balloon having a radiopaque quality.

3.17 The balloon of paragraph 3.16, wherein the winding comprises a radiopaque filament.

3.18 The balloon of any of the foregoing paragraphs, wherein the radiopaque identifier comprises a helical pattern or a diamond pattern.

3.19 A catheter including the balloon of any of the foregoing paragraphs.

3.20 An inflatable balloon for use in connection with a catheter comprising a radiopaque identifier comprising a helical pattern or a diamond pattern.

4.1 A balloon catheter for use in connection with a guidewire, comprising: an elongated, tubular shaft extending in a longitudinal direction, said shaft having a proximal end and a distal end; an inflatable balloon supported along the distal end of the shaft, the balloon when inflated including first and second spaced ends and a working surface between the ends; and at least one wire including at least a radiopaque portion for identifying the location of working surface of the balloon.

4.2 The catheter of paragraph 4.1, wherein said wire comprises a material having a shape memory for adjusting between a first state and a second state.

4.3 The catheter of paragraph 4.1 or 4.2, wherein the at least one wire extends generally in the longitudinal direction.

4.4 The catheter of any of the foregoing paragraphs 4.1 to 4.3, wherein the radiopaque portion is elongated.

4.5 The catheter of any of the foregoing paragraphs 4.1 to 4.4, wherein the wire at least partially comprises a polymer.

4.6 The catheter of any of the foregoing paragraphs 4.1 to 4.5, wherein the at least one wire is at least partially elastic.

4.7 The catheter of any of the foregoing paragraphs 4.1 to 4.6, comprising: a plurality of wires extending generally in the longitudinal direction, at least one of the wires including at least a radiopaque portion for identifying the location of working surface of the balloon.

4.8 The catheter of any of the foregoing paragraphs 4.1 to 4.7, wherein at least one wire extends along an outer surface of the balloon.

4.9 The catheter of any of the foregoing paragraphs 4.1 to 4.8, wherein at least one wire extends along an inner surface of the balloon.

4.10 The catheter of any of the foregoing paragraphs 4.1 to 4.9, wherein at least one wire extends from the first end to the second end of the balloon.

4.11 The catheter of any of the foregoing paragraphs 4.1 to 4.10, wherein the radiopaque portion of at least one wire extends along a portion of the balloon corresponding to the working surface.

4.12 The catheter of any of the foregoing paragraphs 4.1 to 4.11, wherein the radiopaque portion of at least one wire extends along other than along the portion of the balloon corresponding to the working surface.

4.13 The catheter of paragraph 4.7 or any of paragraphs 4.8 to 4.12 as dependent on paragraph 4.7, wherein the wires are spaced substantially equidistantly around a circumference of the balloon.

4.14 The catheter of any of the foregoing paragraphs 4.1 to 4.13, wherein the wire includes a compliant or semi-compliant portion.

4.15 The catheter of any of the foregoing paragraphs 4.1 to 4.14, wherein at least one end of the at least partially radiopaque wire is attached to a bond connecting the balloon to the shaft.

4.16 The catheter of any of the foregoing paragraphs 4.1 to 4.15, further including a drug provided on the balloon.

4.17 The catheter of any of the foregoing paragraphs 4.1 to 4.16, wherein at least one wire at least partially comprises a material having a shape memory for adjusting between a first state and a second state.

4.18 The catheter of paragraph 4.2 or 4.17, wherein the shape memory material comprises NITINOL.

5.1 A balloon catheter adapted for use with a guidewire, comprising: an elongated, tubular shaft extending in a longitudinal direction, said shaft having a proximal end and a distal end; an inflatable balloon supported along the distal end of the shaft, the balloon when inflated including first and second spaced ends and a working surface between the ends; and an insert located within the interior compartment of the balloon, the insert including at least a radiopaque portion separate from the shaft.

5.2 The catheter of paragraph 5.1, wherein the insert is adapted for moving relative to the shaft.

5.3 The catheter of paragraph 5.1 or 5.2, wherein the insert extends from a first end of the balloon to one end of the working surface.

5.4 The catheter of any of the foregoing paragraphs 5.1 to 5.3, wherein the insert comprises a tube made at least partially of a radiopaque material.

5.5 The catheter of any of the foregoing paragraphs 5.1 to 5.4, wherein the insert comprises at least one finger.

5.6 The catheter of paragraph 5.5, wherein the finger includes a radiopaque end portion.

5.7 The catheter of any of the foregoing paragraphs 5.1 to 5.6, wherein the insert comprises a plurality of fingers adapted for moving from a retracted condition to an expanded condition when the balloon is inflated.

5.8 The catheter of any of the foregoing paragraphs 5.1 to 5.7, further including a retractable sheath at least partially covering the insert.

5.9 The catheter of any of the foregoing paragraphs 5.1 to 5.8, wherein the insert comprises a wire.

5.10 The catheter of paragraph 5.9, wherein the wire includes a radiopaque portion corresponding to the working surface.

5.11 The catheter of paragraph 5.10, wherein the wire extends from the first end to the second end of the balloon, and the radiopaque portion comprises an intermediate portion of the wire.

5.12 The catheter of paragraph 5.10 or 5.11, wherein the wire extends from the first end to the second end of the balloon, and the radiopaque portion comprises an end portion of the wire.

5.13 The catheter of any of the foregoing paragraphs 5.1 to 5.12, wherein at least one end of the insert is connected at a location where the balloon connects to the tubular shaft.

5.14 The catheter of any of the foregoing paragraphs 5.1 to 5.13, wherein the insert comprises an annular band.

5.15 The catheter of any of the foregoing paragraphs 5.1 to 5.14, wherein the insert includes perforations.

5.16 The catheter of any of the foregoing paragraphs 5.1 to 5.15, wherein the insert comprises a material having a shape memory.

5.17 The catheter of any of the foregoing paragraphs 5.1 to 5.16, further including a drug on the balloon.

6.1 A parison for being blow molded into a medical balloon for a catheter, comprising: a first tubular layer having a functional modification, and a second tubular layer adapted for bonding with the first tubular layer to form the blow molded balloon.

6.2 The parison of paragraph 6.1, wherein the first layer is external to the second layer.

6.3 The parison of paragraph 6.1, wherein the first layer is internal to the second layer.

6.4 The parison of any of the foregoing paragraphs, wherein the functional modification comprises a radiopaque strip.

6.5 The parison of paragraph 6.4, wherein the strip comprises a circumferential band.

6.6 The parison of paragraph 6.4 or 6.5, wherein the strip extends between a first end and a second end of the first layer.

6.7 The parison of any of the foregoing paragraphs, wherein the first tubular layer is spaced from the second tubular layer.

6.8 The parison of any of the foregoing paragraphs, wherein the functional modification is selected from the group consisting of an added radiopacifier, a surface pattern, an etching, one or more perforations, and combinations of the foregoing.

6.9 A medical balloon formed by the parison of any of the foregoing paragraphs, comprising: a tubular, inflatable body comprising a wall, the body including first and second generally conical ends and a generally cylindrical barrel section between the generally conical ends and providing a working surface.

6.10 The balloon of paragraph 6.9, wherein the first layer extends from the first end to the second and of the balloon.

6.11 The balloon of paragraph 6.9, wherein the first layer extends along only the working surface.

6.12 The balloon of any of paragraphs 6.9 to 6.11, wherein the first layer extends along an entire circumference of a portion of the wall.

6.13 The balloon of any of paragraphs 6.9 to 6.12, wherein the first layer extends along the full circumference of the wall.

6.14 The balloon of any of paragraphs 6.9 to 6.13, wherein the wall includes first and second spaced shoulders, and wherein the first layer is positioned between the shoulders.

6.15 The balloon of any of paragraphs 6.9 to 6.14, wherein the first and second layers both extend from a first end to a second end of the balloon.

6.16 The balloon of any of paragraphs 6.9 to 6.15, further comprising an at least partially radiopaque tube positioned over the barrel section and extending substantially along the working surface.

6.17 The balloon of paragraph 6.16, further including first and second shoulders adjacent the proximal and distal ends of the radiopaque tube.

6.18 The balloon of paragraph 6.16 or 6.17, wherein the entire tube is radiopaque.

7.1 A balloon catheter, comprising: an elongated, tubular shaft having a proximal end and a distal end; and a balloon positioned along the distal end of the shaft, a portion of a wall of the balloon partially comprising a coextruded radiopaque material.

7.2 The catheter of paragraph 7.1, wherein the radiopaque portion comprises at least one strip extending along a working surface of the balloon.
7.3 The catheter of paragraph 7.1 or 7.2, wherein the radiopaque portion comprises at least one strip extending along a full length surface of the balloon.
7.4 The catheter of any of paragraphs 7.1 to 7.3, wherein the radiopaque portion comprises at least one strip extending along a first cone section of the balloon.
7.5 The catheter of paragraph 7.4, wherein the radiopaque portion comprises at least one strip extending along a second cone section of the balloon.
7.6 The catheter of any of paragraphs 7.1 to 7.5, wherein the balloon includes a plurality of radiopaque portions.
7.7 The catheter of paragraph 7.6, wherein each of the plurality of radiopaque portions comprises a longitudinal strip.
7.8 The catheter of paragraph 7.7, wherein the strips extend at least along a working surface of the balloon.
7.9 The catheter of any of paragraphs 7.6 to 7.8, wherein the plurality of radiopaque portions are spaced apart in a circumferential direction.
7.10 The catheter of any of the foregoing paragraphs 7.1 to 7.9, wherein the balloon includes a barrel section and conical sections at each end of the barrel section, and wherein the radiopaque portion is provided on the barrel section.
7.11 The catheter of any of the foregoing paragraphs 7.1 to 7.10, wherein the balloon includes a barrel section and conical sections at each end of the barrel section, and wherein the radiopaque portion is provided on one or both of the cone sections.
7.12 The catheter of any of the foregoing paragraphs 7.1 to 7.11, wherein the radiopaque portion comprises a layer of the balloon wall.
7.13 The catheter of paragraph 7.12, wherein the layer comprises an inner layer.
7.14 The catheter of paragraph 7.12 or 7.13, wherein the layer comprises an outer layer.
7.15 The catheter of paragraph 7.14, wherein the outer layer is etched.
7.16 The catheter of any of paragraphs 7.12 to 7.15, wherein the balloon includes a barrel section and conical sections at each end of the barrel section, and the layer extends along the entire barrel section.
7.17 The catheter of any of paragraphs 7.12 to 7.16, wherein the balloon includes a barrel section and conical sections at each end of the barrel section, and the layer extends along the entirety of one or both of the conical sections.
7.18 The catheter of any of the foregoing paragraphs 7.1 to 7.17, wherein all portions of the wall comprise coextruded radiopaque material.
7.19 The catheter of any of the foregoing paragraphs 7.1 to 7.18, further including a drug on the balloon.
7.20 The catheter of any of the foregoing paragraphs 7.1 to 7.19, wherein the radiopaque material comprises ePTFE.
8.1 A balloon catheter, comprising: a shaft extending in a longitudinal direction, said shaft having a proximal end and a distal end, and supporting at least one radiopaque identifier; an inflatable balloon supported along the distal end of the shaft, the balloon when inflated including a working surface; and an actuator for aligning at least one end of the working surface with the at least one radiopaque identifier.
8.2 The catheter of paragraph 8.1, wherein the actuator includes a first position corresponding to a deflated state of the balloon and a second position corresponding to the inflated state of the balloon.
8.3 The catheter of paragraph 8.1 or 8.2, wherein the actuator comprises a spring.
8.4 The catheter of any of the foregoing paragraphs 8.1 to 8.3, wherein the spring comprises a leaf spring.
8.5 The catheter of any of the foregoing paragraphs 8.1 to 8.4, wherein the actuator comprises a plurality of springs spaced circumferentially about the catheter.
8.6 The catheter of any of the foregoing paragraphs 8.1 to 8.5, wherein a first portion of the actuator is fixed to the balloon and a second portion of the actuator is adapted for movement relative to the shaft.
8.7 The catheter of paragraph 8.6, wherein the first portion of the actuator is captured between two layers on the wall of the balloon.
8.8 The catheter of paragraph 8.6 or 8.7, wherein the shaft includes a channel for at least partially receiving the second portion of the actuator.
8.9 The catheter of any of the foregoing paragraphs 8.1 to 8.8, further including a stop for stopping the movement of the actuator.
8.10 The catheter of any of the foregoing paragraphs 8.1 to 8.9, wherein the radiopaque identifier comprises a marker attached to the shaft.
8.11 The catheter of any of the foregoing paragraphs 8.1 to 8.10, wherein the radiopaque identifier comprises an insert positioned within the interior compartment of the balloon.
8.12 The catheter of any of the foregoing paragraphs 8.1 to 8.11, wherein the actuator is a first actuator for aligning a distal end of the working surface with the radiopaque identifier, and further including a second actuator for aligning a proximal end of the working surface with the radiopaque identifier.
8.13 The catheter of paragraph 8.12, wherein each of the first and second actuators comprise a plurality of springs.
8.14 The catheter of any of the foregoing paragraphs, wherein the radiopaque identifier comprises a first marking and a second marking, and wherein the actuator is a first actuator for aligning a distal end of the working surface with the first marking, and further including a second actuator for aligning a proximal end of the working surface with the second marking.
8.15 The balloon catheter of any of the foregoing paragraphs 8.1 to 8.14, comprising: a shaft extending in a longitudinal direction, said shaft having a proximal end and a distal end, and supporting first and second radiopaque identifiers; a first actuator for aligning a first end of the working surface with the first radiopaque marking; and a second actuator for aligning a second end of the working surface with the second radiopaque identifier.
8.16 The balloon catheter of any of the foregoing paragraphs 8.1 to 8.15, comprising: a shaft for carrying the balloon, the shaft including at least one channel formed in an outer portion of a wall of the shaft; and an actuator having a first end connected to the balloon and a second end at least partially positioned in the channel.
8.17 The balloon catheter of any of the foregoing paragraphs 8.1 to 8.16, comprising: a shaft for carrying the balloon, the shaft including a plurality of channels formed in an outer portion of the wall of the shaft.
8.18 The catheter of paragraph 8.17, further including an actuator having a first end connected to the balloon and a second end positioned in at least one of the channels.
8.19 The catheter of any of the foregoing paragraphs 8.1 to 8.8, comprising: a spring connected to a wall of the balloon.
8.20 The catheter of paragraph 8.19, wherein the spring is at least partially radiopaque.

8.21 The catheter of paragraph 8.19 or 8.20, wherein the spring is connected to a conical section of the wall of the balloon.

8.22 The balloon catheter of any of the foregoing paragraphs 8.1 to 8.21, wherein the balloon includes a drug.

9.1 A balloon catheter for use with a guidewire, comprising: an elongated, tubular shaft extending in a longitudinal direction, said shaft having a proximal end and a distal end; an inflatable balloon connected to the distal end of the shaft, the balloon including a working surface; a radiopaque identifier for identifying the working surface; and a receiver adjacent the proximal end of the shaft and adapted for allowing the shaft to move relative to the receiver in at least the longitudinal direction.

9.2 The catheter of paragraph 9.1, wherein the shaft carries a stop, and the receiver further includes a recess for receiving the stop, said recess having a dimension in the longitudinal direction that is greater than a corresponding dimension of the stop.

9.3 The catheter of paragraph 9.2, further including a tube for supplying an inflation fluid to inflate the balloon, said tube being connected to the receiver and generally coaxial with the shaft, and wherein the stop forms a seal with the recess to prevent the inflation fluid from passing around the shaft.

9.4 The catheter of paragraph 9.3, wherein the seal comprises an O-ring arranged coaxially with the shaft.

9.5 The catheter of paragraph 9.1, wherein the radiopaque identifier is separate from the shaft.

9.6 The catheter of paragraph 9.5, wherein the radiopaque identifier comprises an insert positioned within the interior compartment of the balloon.

9.7 The catheter of paragraph 9.6, wherein the insert comprises a tubular sleeve arranged coaxially with the shaft.

9.8 The catheter of paragraph 9.6, wherein the insert comprises a first insert at a proximal end of the balloon and a second insert at a distal end of the balloon.

9.9 The catheter of paragraph 9.1, further including a guidewire for positioning in the shaft.

9.10 A hub for a balloon catheter having an elongated, tubular shaft extending in a longitudinal direction, said shaft having a proximal end and a distal end, and an inflatable balloon connected to the distal end of the shaft for being inflated by an inflation fluid, comprising: a body including a receiver for receiving a proximal portion of the shaft and adapted for allowing the shaft to move relative to the receiver in at least the longitudinal direction; and a stop for restraining the movement of the shaft relative to the body in the longitudinal direction.

9.11 The hub of paragraph 9.10, wherein the body includes a guidewire port arranged in communication with the receiver, and further including an inflation port for introducing the inflation fluid for inflating the balloon.

9.12 The hub of paragraph 9.10, wherein the receiver further includes a recess for receiving the stop, said recess having a dimension in the longitudinal direction that is greater than a corresponding dimension of the stop.

9.13 The hub of paragraph 9.12, wherein the stop forms a seal with the recess to prevent the inflation fluid from passing.

9.14 The hub of paragraph 9.10, wherein the stop comprises an O-ring.

9.15 A catheter including a guidewire shaft having a distal end connected to a balloon and at a proximal end mounted for sliding movement.

9.16 The catheter of any of the foregoing paragraphs, further including a drug on the balloon.

9.17 A catheter comprising a hub for receiving a proximal end of a guidewire shaft, the shaft being adapted to slidably move in a restrained manner relative to the hub.

10.1 A balloon catheter, comprising: an elongated tubular shaft having a proximal end and a distal end spaced apart in a longitudinal direction, the shaft along a distal portion including at least one radiopaque identifier, said distal portion being formed of a material resistant to elongation in the longitudinal direction; and an inflatable, non-compliant balloon extending over the distal portion of the shaft.

10.2 The catheter according to paragraph 10.1, wherein the balloon includes a generally cylindrical barrel section positioned between generally conical sections, said barrel section including a working surface having at least one edge aligned with the radiopaque identifier.

10.3 The catheter according to paragraph 10.2, wherein the radiopaque identifier comprises a first marker positioned at the at least one edge of the working surface, and further including a second marker positioned at the opposite edge of the working surface in the longitudinal direction.

10.4 The catheter according to paragraph 10.2, wherein each marker comprises a radiopaque band swaged to the distal portion of the shaft.

10.5 The catheter according to paragraph 10.1, wherein the distal portion of the shaft comprises a tube adapted for guiding a guidewire from a proximal end of the balloon to a distal end of the balloon.

10.6 The catheter according to paragraph 10.1, wherein at least the distal portion of the shaft comprises steel.

10.7 The catheter according to paragraph 10.1, wherein the shaft comprises steel.

10.8 The catheter according to paragraphs 10.6 or 10.7, wherein the steel shaft comprises a stainless steel.

10.9 The catheter according to paragraphs 10.7 or 10.8, wherein the steel shaft includes a spiral cut along a portion other than the distal portion covered by the balloon.

10.10 The catheter according to paragraphs 10.7 or 10.8, wherein the steel shaft comprises a polymer layer.

10.11 The catheter according to paragraph 10.10, wherein the polymer layer comprises an outer layer of the shaft.

10.12 The catheter according to paragraph 10.1, wherein the distal portion of the shaft comprises a polymer shaft including a braid or mesh.

10.13 The catheter according to paragraph 10.1, wherein the balloon includes a generally cylindrical barrel section positioned between generally conical sections, the distal portion of the shaft extending from a first end of a first conical section to a second end of a second conical section.

10.14 The catheter according to paragraph 10.1, wherein the non-compliant balloon comprises one or more inelastic fibers.

10.15 The catheter according to paragraph 10.1, wherein the non-compliant balloon comprises polyethylene terephthalate.

10.16 The catheter of any of the foregoing paragraphs 10.1 to 10.15, further including a drug on the balloon.

11.1 A balloon catheter, comprising: a shaft extending in a longitudinal direction and adapted for expanding from a compressed condition to an expanded condition in the longitudinal direction, the shaft supporting at least one radiopaque identifier; and an inflatable balloon positioned along the shaft, the balloon when inflated including a working surface for aligning with the radiopaque identifier in at least the expanded condition of the shaft.

11.2 The catheter of paragraph 11.1, wherein the expandable shaft comprises a first portion connected in tandem to an expandable element.

11.3 The catheter of paragraphs 11.1 or 11.2, wherein the expandable element comprises a spring.
11.4 The catheter of paragraph 11.3, wherein the spring comprises a coil spring.
11.5 The catheter of paragraphs 11.3 or 11.4, wherein the spring comprises a tension coil spring.
11.6 The catheter of paragraph 11.2, wherein the expandable element comprises a bellows.
11.7 The catheter of paragraph 11.2, wherein the expandable element comprises a fiber matrix.
11.8 The catheter of paragraph 11.7, further including a spring associated with the fiber matrix.
11.9 The catheter of any of paragraphs 11.2-11.8, wherein the expandable element is inside an interior compartment of the balloon.
11.10 The catheter of any of paragraphs 11.2-11.8, wherein the expandable element is outside an interior compartment of the balloon.
11.11 The catheter of any of paragraphs 11.2-11.10, wherein the expandable element connects to one end of the balloon.
11.12 The catheter of any of paragraphs 11.2-11.10, wherein the expandable element connects the first portion of the shaft to a second portion of the shaft.
11.13 The catheter of any of the foregoing paragraphs 11.1 to 11.12, wherein the shaft comprises an inflation lumen for delivering an inflation fluid to the balloon.
11.14 The catheter of any of the foregoing paragraphs 11.1 to 11.13, wherein the expandable shaft in at least a partially expanded condition a port for delivering the inflation fluid to the balloon, said port being closed when the shaft is in a non-expanded condition.
11.15 The catheter of any of the foregoing paragraphs 11.1 to 11.14, wherein the expandable shaft comprises a first expandable element connecting a first portion of the shaft to a second portion of the shaft, and further including a second expandable element connecting the second portion of the shaft to a third portion of the shaft.
11.16 The catheter of paragraph 11.15, wherein the first and second expandable elements comprise first and second coil springs.
11.17 The catheter of paragraph 11.16, wherein the first and second coil springs have different spring constants.
11.18 The catheter of any of the foregoing paragraphs 11.1 to 11.17, wherein the radiopaque identifier comprises a pair of spaced radiopaque markers, one positioned in alignment with a first end of the working surface and another positioned at a second end of the working surface.
11.19 The catheter of any of paragraphs 11.15-11.18, wherein the first and second expandable elements comprise a radiopaque material.
11.20 The catheter of any of the foregoing paragraphs 11.1 to 11.19, wherein the radiopaque identifier comprises a spring.
11.21 The catheter of paragraph 11.2, wherein the expandable element comprises a spring having a variable spring constant.
11.22 The catheter of any of the foregoing paragraphs 11.1 to 11.21, wherein the shaft comprises a guidewire lumen.
11.23 The catheter of any of the foregoing paragraphs 11.1 to 11.22, further including a passage adjacent the tip for receiving a guidewire external to the balloon.
11.24 The catheter of paragraph 11.2, wherein the first portion is adjacent a distal end of the shaft.
11.25 A balloon catheter, comprising: a shaft; a balloon; and an expandable element adapted for expanding in the longitudinal direction connecting the shaft to the balloon.

11.26 The catheter of paragraph 11.25, wherein the expandable element is selected from the group consisting of a spring, a bellows, a fiber matrix, or combinations of the foregoing.
11.27 The catheter of paragraph 11.25 or 26, wherein the expandable element comprises an encapsulated spring.
11.28 A balloon catheter comprising a balloon and an inflation lumen including an expandable element adapted for expanding in the longitudinal direction for providing a fluid to the balloon.
11.29 The catheter of any of paragraphs 11.25-11.28, wherein the expandable element comprises a radiopaque material.
11.30 The catheter of any of the foregoing paragraphs 11.1 to 11.29, further including a drug on the balloon.
12.1 A balloon catheter, comprising: an elongated, tubular shaft extending in a longitudinal direction, said shaft having a proximal end and a distal end; and a balloon having an inflation compartment formed a balloon wall including a working surface, and further including at least one chamber adjacent to the working surface adapted for receiving an identifier for identifying the location of the working surface.
12.2 The balloon catheter of paragraph 12.1, wherein the shaft includes a first lumen for supplying a fluid to the chamber.
12.3 The balloon catheter of paragraph 12.2, wherein the shaft includes a port between the first lumen and the chamber.
12.4 The balloon catheter of paragraph 12.2, wherein the shaft includes a second lumen for supplying a fluid to an interior compartment of the balloon.
12.5 The balloon catheter of paragraph 12.4, wherein the shaft includes a port between the second lumen and the interior compartment.
12.6 The balloon catheter of any of the foregoing paragraphs 12.1 to 12.5, wherein the identifier comprises a contrast agent.
12.7 The balloon catheter of any of the foregoing paragraphs 12.1 to 12.6, wherein the contrast agent comprises a material selected from the group consisting of a radiopacifier, polyvinyl acetate, cellulose, a fluid, a liquid, a solid, a powder, or combinations of the foregoing.
12.8 The balloon catheter of any of the foregoing paragraphs 12.1 to 12.7, wherein the chamber comprises a first chamber at a proximal end of the balloon, and further including a second chamber at a distal end of the balloon.
12.9 The balloon catheter of paragraph 12.8, wherein the second chamber is adapted for receiving the identifier from a lumen in the shaft in fluid communication with the first chamber via a port.
12.10 The balloon catheter of any of the foregoing paragraphs 12.1 to 12.9, wherein the chamber is generally annular.
12.11 The balloon catheter of any of the foregoing paragraphs 12.1 to 12.10, wherein the chamber is positioned between a transition from a barrel section to a conical section of the balloon and an end of the balloon.
12.12 The balloon catheter of any of the foregoing paragraphs 12.1 to 12.11, wherein the chamber is provided by a film attached to the balloon wall.
12.13 The balloon catheter of any of the foregoing paragraphs 12.1 to 12.12, wherein the chamber is embedded in the balloon wall.
12.14 The balloon catheter of any of the foregoing paragraphs 12.1 to 12.13, wherein the chamber is provided by a film extending between the balloon wall and an outer surface of the shaft.

While the disclosure presents certain embodiments to illustrate the inventive concepts, numerous modifications, alterations, and changes to the described embodiments are possible without departing from the sphere and scope of the present invention, as defined in the appended claims. For example, any ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Accordingly, it is intended that the present invention not be limited to the described embodiments, but that it has the full scope defined by the language of the following claims, and equivalents thereof.

The invention claimed is:

1. A method of manufacturing an at least partially radiopaque balloon, comprising:
    blow molding a first layer of a material having a functional modification and a second layer of material together to form the balloon;
    wherein the blow molding step comprises providing the first layer along an outer surface of the second layer; and
    wherein an outer surface of the first layer comprises the functional modification.

2. The method of claim 1, further including the step of providing the first layer of material that is shorter that the second layer of material in a longitudinal direction.

3. The method of claim 1, further including the step of providing the first layer with a radiopaque portion in the form of at least one strip.

4. The method of claim 1, further including the step of providing the first layer with a substantially continuous radiopacity.

5. The method claim 1, further including the step of providing the first layer with the functional modification selected from the group consisting of an added radiopacifier, a surface pattern, an etching, one or more perforations, and combinations of the foregoing.

6. A method of manufacturing a medical balloon using a mold having a mold cavity, comprising:
    blow molding a parison at least partially within the mold cavity of the mold to form a balloon having a modified outer portion along a working surface of the balloon;
    wherein the blow molding step is preceded by the step of providing a fenestrated tube for forming the modified portion in the blow mold.

7. A method of manufacturing a medical balloon using a mold having a mold cavity, comprising:
    blow molding a parison at least partially within the mold cavity of the mold to form a balloon having a modified outer portion along a working surface of the balloon;
    wherein the blow molding step is preceded by the step of providing a reticulated tube for forming the modified portion in the blow mold.

* * * * *